(12) United States Patent
Govari et al.

(10) Patent No.: US 9,445,725 B2
(45) Date of Patent: Sep. 20, 2016

(54) IRRIGATED CATHETER TIP WITH TEMPERATURE SENSOR ARRAY

(71) Applicant: BIOSENSE WEBSTER (ISRAEL), LTD., Yokneam (IL)

(72) Inventors: Assaf Govari, Haifa (IL); Christopher Thomas Beeckler, Brea, CA (US); Athanassios Papaioannou, Los Angeles, CA (US); Rowan Olund Hettel, Redondo Beach, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 12 days.

(21) Appl. No.: 13/716,578

(22) Filed: Dec. 17, 2012

(65) Prior Publication Data

US 2014/0171821 A1 Jun. 19, 2014

(51) Int. Cl.
*A61B 5/01* (2006.01)
*A61B 18/14* (2006.01)
(Continued)

(52) U.S. Cl.
CPC ............... *A61B 5/01* (2013.01); *A61B 5/4836* (2013.01); *A61B 5/6852* (2013.01);
(Continued)

(58) Field of Classification Search
CPC .......... A61B 2017/00084; A61B 2017/00088; A61B 2017/00092; A61B 2017/00097; A61B 2017/00101; A61B 18/1492; A61B 2018/00577; A61B 2018/00791; A61B 2018/00797; A61B 5/01; A61B 5/6852; A61B 5/4836; A61N 1/056; A61N 1/06; A61N 1/05; A61M 25/0069; A61M 25/0009

USPC ....... 600/547, 549; 606/33, 41; 607/99, 102, 607/113
See application file for complete search history.

(56) References Cited

U.S. PATENT DOCUMENTS

| 4,945,305 A | 7/1990 | Blood |
| 5,170,566 A | 12/1992 | Fowler |

(Continued)

FOREIGN PATENT DOCUMENTS

| EP | 1530057 B1 | 5/2005 |
| EP | 1922991 B1 | 5/2008 |

(Continued)

OTHER PUBLICATIONS rib. (n.d.). Dictionary.com Unabridged. Retrieved Aug. 15, 2014, from Dictionary.com website: http://dictionary.reference.com/browse/rib.*

(Continued)

*Primary Examiner* — Jeffrey G Hoekstra
*Assistant Examiner* — David J McCrosky
(74) *Attorney, Agent, or Firm* — Wayne C. Jaeschke, Jr.

(57) ABSTRACT

A medical probe includes an insertion tube having a distal end configured for insertion into a body of a patient and containing a lumen for conveying an irrigation fluid and an electrical conductor for conveying electrical energy. A conductive cap is attached to the distal end of the insertion tube and coupled electrically to the electrical conductor. The conductive cap has an outer surface perforated by multiple apertures and defines an inner cavity in fluid communication with the lumen of the insertion tube so as to permit the irrigation fluid from the lumen to flow out of the cap through the apertures. A plurality of temperature sensors are mounted within the conductive cap in thermal communication with the outer surface and are thermally insulated from the irrigation fluid in the inner cavity.

2 Claims, 3 Drawing Sheets

(51) Int. Cl.
*A61B 5/00* (2006.01)
*A61M 25/00* (2006.01)
*A61N 1/05* (2006.01)
*A61B 18/00* (2006.01)

(52) U.S. Cl.
CPC ..... *A61B 18/1492* (2013.01); *A61M 25/0009* (2013.01); *A61M 25/0069* (2013.01); *A61N 1/05* (2013.01); *A61B 2018/00029* (2013.01); *A61B 2018/00351* (2013.01); *A61B 2018/00357* (2013.01); *A61B 2018/00678* (2013.01); *A61B 2018/00702* (2013.01); *A61B 2018/00744* (2013.01); *A61B 2018/00797* (2013.01); *A61B 2018/00815* (2013.01); *A61B 2018/00821* (2013.01); *A61B 2218/002* (2013.01); *Y10T 29/49117* (2015.01)

(56) References Cited

U.S. PATENT DOCUMENTS

| | | | |
|---|---|---|---|
| 5,391,199 A | | 2/1995 | Ben-Haim |
| 5,433,708 A * | | 7/1995 | Nichols et al. ............... 604/113 |
| 5,435,308 A * | | 7/1995 | Gallup et al. ................. 600/342 |
| 5,443,489 A | | 8/1995 | Ben-Haim |
| 5,453,686 A | | 9/1995 | Anderson |
| 5,688,267 A | | 11/1997 | Panescu |
| 5,755,715 A | | 5/1998 | Stern et al. |
| 5,853,409 A | | 12/1998 | Swanson et al. |
| 5,957,961 A | | 9/1999 | Maguire et al. |
| 6,030,379 A | | 2/2000 | Panescu et al. |
| 6,063,078 A | | 5/2000 | Wittkampf |
| 6,073,043 A | | 6/2000 | Schneider |
| 6,176,857 B1 | | 1/2001 | Ashley |
| 6,217,574 B1 | | 4/2001 | Webster |
| 6,239,724 B1 | | 5/2001 | Doron |
| 6,293,943 B1 | | 9/2001 | Panescu et al. |
| 6,312,425 B1 | | 11/2001 | Simpson |
| 6,371,379 B1 | | 4/2002 | Dames |
| 6,391,024 B1 | | 5/2002 | Sun |
| 6,427,079 B1 | | 7/2002 | Schneider |
| 6,427,314 B1 | | 8/2002 | Acker |
| 6,500,172 B1 | | 12/2002 | Panescu et al. |
| 6,549,004 B1 | | 4/2003 | Prigge |
| 6,616,657 B2 | | 9/2003 | Simpson et al. |
| 6,618,612 B1 | | 9/2003 | Acker |
| 6,638,275 B1 | | 10/2003 | McGaffigan et al. |
| 6,679,906 B2 * | | 1/2004 | Hammack et al. ........... 607/105 |
| 6,689,127 B1 | | 2/2004 | Gough et al. |
| 6,690,963 B2 | | 2/2004 | Ben-Haim |
| 6,730,077 B2 | | 5/2004 | Carroll |
| 7,047,068 B2 | | 5/2006 | Haissaguerre |
| 7,094,215 B2 | | 8/2006 | Davison et al. |
| 7,981,147 B2 * | | 7/2011 | Korb et al. ..................... 607/96 |
| 2002/0065455 A1 | | 5/2002 | Ben-Haim |
| 2003/0117270 A1 | | 6/2003 | Dimmer |
| 2003/0120150 A1 | | 6/2003 | Govari |
| 2004/0068178 A1 | | 4/2004 | Govari |
| 2007/0203481 A1 * | | 8/2007 | Gregg et al. .................... 606/34 |
| 2007/0287998 A1 | | 12/2007 | Sharareh |
| 2008/0161797 A1 * | | 7/2008 | Wang et al. .................... 606/41 |
| 2009/0138007 A1 | | 5/2009 | Govari |
| 2009/0149848 A1 * | | 6/2009 | Werneth et al. ................ 606/33 |
| 2009/0156921 A1 | | 6/2009 | Wang |
| 2009/0306649 A1 * | | 12/2009 | Mest .................. A61B 18/1492 606/41 |
| 2010/0030209 A1 | | 2/2010 | Govari et al. |
| 2010/0160904 A1 | | 6/2010 | McMilliam |
| 2011/0066147 A1 * | | 3/2011 | He et al. ......................... 606/33 |
| 2011/0224664 A1 | | 9/2011 | Bar-Tal et al. |
| 2011/0224667 A1 | | 9/2011 | Koblish et al. |
| 2012/0172717 A1 * | | 7/2012 | Gonda .......................... 600/424 |
| 2012/0265062 A1 | | 10/2012 | Sliwa et al. |
| 2013/0204134 A1 | | 8/2013 | Harks |

FOREIGN PATENT DOCUMENTS

| | | |
|---|---|---|
| EP | 2526887 A1 | 11/2012 |
| WO | 96/05768 A1 | 2/1996 |

OTHER PUBLICATIONS

Cap. (n.d.). Retrieved Aug. 15, 2014, from http://www.merriam-webster.com/dictionary/cap.*
Dictionary.com, "integrally," in Dictionary.com Unabridged. Random House, Inc. Retrieved from <http://dictionary.reference.com/browse/integrally> on Apr. 1, 2015.*
McGreevy, K.S. et al. Comparison of a Saline Irrigated Cooled-Tip Catheter to Large Electrode Catheters With Single and Multiple Temperature Sensors for Creation of Large Radiofrequency Lesions. Journal of Interventional Cardiac Electrophysiology 14, 139-145, 2005.
European Search Report, Application No. 13197467.7, 6 pages, dated Mar. 19, 2014.
EP Search Report, EP Application 14 19 4536 Dated Apr. 22, 2015.
U.S. Appl. No. 12/627,327, filed Nov. 20, 2009.
U.S. Appl. No. 13/716,578, filed Dec. 17, 2012.

* cited by examiner

IRRIGATED CATHETER TIP WITH TEMPERATURE SENSOR ARRAY

FIELD OF THE INVENTION

The present invention relates generally to invasive medical devices, and particularly to probes used in ablating tissue within the body.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

It has been found that cooling the area of the ablation site reduces tissue charring and thrombus formation. For this purpose, for example, Biosense Webster Inc. (Diamond Bar, Calif.) offers the ThermoCool® irrigated-tip catheter for use with its CARTO® integrated mapping and ablation system. The metal catheter tip, which is energized with radio-frequency (RF) electrical current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue.

U.S. Patent Application Publication 2010/0030209, whose disclosure is incorporated herein by reference, describes a catheter with a perforated tip, which includes an insertion tube, having a distal end for insertion into a body of a subject. A distal tip is fixed to the distal end of the insertion tube and is coupled to apply energy to tissue inside the body. The distal tip has an outer surface with a plurality of perforations through the outer surface, which are distributed circumferentially and longitudinally over the distal tip. A lumen passes through the insertion tube and is coupled to deliver a fluid to the tissue via the perforations.

Some ablation catheters include sensors for monitoring temperature during the ablation procedure. For example, U.S. Pat. No. 5,957,961 describes a catheter having a distal segment carrying at least one electrode extending along the segment and having a number of temperature sensors arranged along the distal segment adjacent the electrode, each providing an output indicative of temperature. The catheter is coupled to a power source, which provides RF energy to the electrode. Temperature processing circuitry is coupled to the temperature sensors and the power source, and controls power output from the power source as a function of the outputs of the temperature sensors.

As another example, U.S. Pat. No. 6,312,425 describes an RF ablation catheter tip electrode with multiple thermal sensors. A tip thermal sensor is located at or near the apex of the distal-end region, and one or more side thermal sensors are located near the surface of the proximal-end region. The electrode is preferably an assembly formed from a hollow dome-shaped shell with a core disposed within the shell. The side thermal sensor wires are electrically connected inside the shell and the core has a longitudinal channel for the side thermal sensor wires welded to the shell. The shell also preferably has a pocket in the apex of the shell, and the end thermal sensor wires pass through the core to the apex of the shell.

SUMMARY

Embodiments of the present invention that are described hereinbelow provide ablation probes with enhanced temperature measurement capabilities.

There is therefore provided, in accordance with an embodiment of the present invention, a medical probe, which includes an insertion tube having a distal end configured for insertion into a body of a patient and containing a lumen for conveying an irrigation fluid and an electrical conductor for conveying electrical energy. A conductive cap is attached to the distal end of the insertion tube and coupled electrically to the electrical conductor. The conductive cap has an outer surface perforated by multiple apertures and defines an inner cavity in fluid communication with the lumen of the insertion tube so as to permit the irrigation fluid from the lumen to flow out of the cap through the apertures. A plurality of temperature sensors are mounted within the conductive cap in thermal communication with the outer surface and are thermally insulated from the irrigation fluid in the inner cavity.

In one embodiment, the cap includes multiple ribs internal to the outer surface, and the temperature sensors are mounted inside the ribs.

In another embodiment, the probe includes an inner wall inside and parallel to the cap, wherein the inner cavity is contained between the inner wall and the cap, and the temperature sensors are mounted between the inner wall and the cap. The probe may include multiple spacers, which are located within the inner cavity and connect the cap to the inner wall, wherein the temperature sensors are mounted in the spacers.

In still another embodiment, the cap includes a side wall having multiple longitudinal bores therein, and the temperature sensors are fitted into and mounted in the bores.

Typically, the temperature sensors are arrayed around the cap at different circumferential and axial positions. The temperature sensors may be arranged in pairs that are axially spaced apart at different circumferential locations.

In a disclosed embodiment, the insertion tube is configured as a catheter for insertion into a heart of the patient, and the conductive cap is configured to contact and apply the electrical energy to myocardial tissue in the heart so as to ablate the myocardial tissue.

There is also provided, in accordance with an embodiment of the present invention, medical apparatus, which include a probe as described above. A pump is coupled to the lumen at the proximal end of the insertion tube so as to supply the irrigation fluid to the probe. A power generator is coupled to the electrical conductor at the proximal end of the insertion tube so as to provide the electrical energy to the conductive cap. Monitoring circuitry is connected to receive temperature signals from the temperature sensors so as to monitor a temperature of the cap.

In a disclosed embodiment, the monitoring circuitry is configured to select a highest temperature reading from among the plurality of the temperature sensors and to control at least one of the pump and the power generator responsively to the highest temperature reading.

There is additionally provided, in accordance with an embodiment of the present invention, a method for medical treatment, which includes inserting a probe, as described above, into a body of a patient. The conductive cap is brought into contact with tissue within the body. Electrical energy is applied via the electrical conductor to the cap so ablate the tissue, while supplying the irrigation fluid via the lumen in order to irrigate the tissue. A temperature of the conductive cap is monitored using the temperature sensors while ablating the tissue.

Inserting the probe may include advancing the probe into a heart of the patient, so as to apply the electrical energy to myocardial tissue.

There is further provided, in accordance with an embodiment of the present invention, a method for producing a medical probe, which includes providing an insertion tube having a distal end configured for insertion into a body of a patient and containing a lumen for conveying an irrigation fluid and an electrical conductor for conveying electrical energy. A conductive cap is formed, having an outer surface perforated by multiple apertures and defining an inner cavity. The conductive cap is attached to the distal end of the insertion tube with the inner cavity in fluid communication with the lumen of the insertion tube so as to permit the irrigation fluid from the lumen to flow out of the cap through the apertures. The conductive cap is coupled electrically to the electrical conductor. A plurality of temperature sensors are mounted within the conductive cap in thermal communication with the outer surface, while thermally insulating the temperature sensors from the irrigation fluid in the inner cavity.

The present invention will be more fully understood from the following detailed description of the embodiments thereof, taken together with the drawings in which:

DETAILED DESCRIPTION OF EMBODIMENTS

Intracardiac ablation procedures are characterized by rapid temperature changes and non-uniform temperature distribution in the tissue and its vicinity. Therefore, the temperature measured by a sensor at the tip of an ablation catheter may not accurately reflect the actual, current temperature in the tissue. Furthermore, when a temperature sensor in a catheter is washed by irrigation fluid, the temperature reading will reflect the fluid temperature, which is generally far cooler than the tissue temperature outside the catheter.

Embodiments of the present invention that are described hereinbelow provide irrigated ablation electrodes with embedded temperature sensors that provide accurate tissue temperature assessment. Such electrodes typically comprise a conductive cap, which is attached to the distal tip of the insertion tube of an invasive probe, such as a cardiac catheter. A cooling fluid flows out through an array of perforations in the electrode to irrigate the tissue under treatment.

The temperature sensors are mounted at different locations in proximity to the outer surface of the electrode. The electrode is constructed so that the sensors are in proximity to and thermal communication with the outer surface, and are thermally insulated from, rather than immersed in, the cooling fluid within the probe. The sensors thus provide multiple temperature readings that are substantially independent of the cooling fluid temperature, at different locations on the tip electrode.

Typically, the sensor that gives the highest temperature reading is the one that is in contact with the tissue being ablated, and the temperature measured by this sensor varies linearly with the actual tissue temperature. (Flow of the cooling fluid through the perforations in the electrode is generally lowest in areas that are in firm contact with the tissue, and the sensors in these areas typically give the highest temperature readings.) The reading from this hottest sensor may thus be used in particular to monitor the tissue temperature and control the applied power and duration of the ablation procedure in order to obtain the desired therapeutic result without excessive tissue damage. Alternatively or additionally, the temperature readings of the multiple sensors can be combined and interpolated to give a map of temperature over the area of the catheter tip.

Although the disclosed embodiments relate specifically to intracardiac catheters and ablation procedures, the principles of the present invention may similarly be applied, mutatis mutandis, to probes of other types, for use in substantially any sort of invasive thermal treatment.

Figure 1:
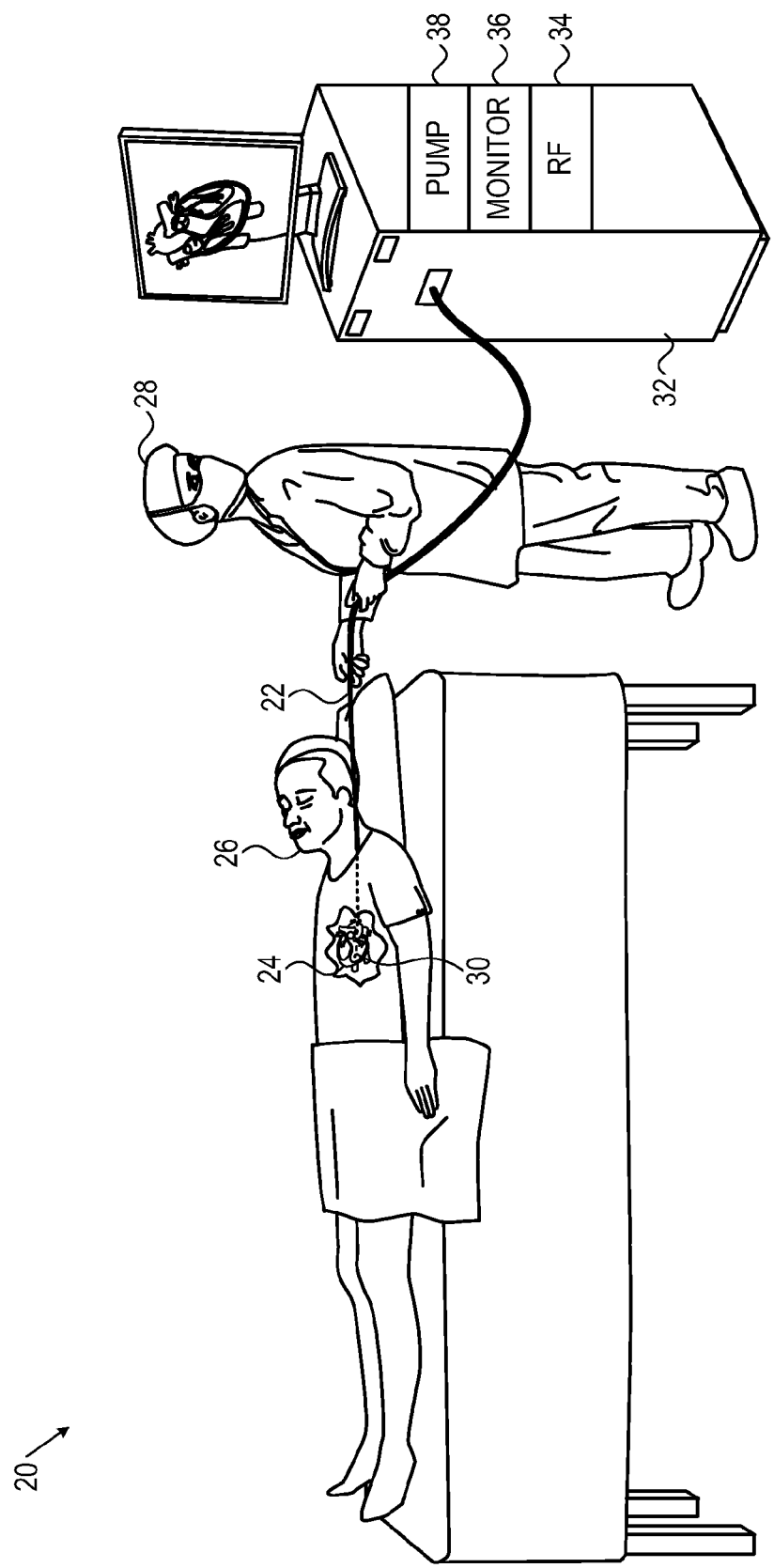
FIG. 1 is a schematic, pictorial illustration of a system for intracardiac ablation, in accordance with an embodiment of the present invention.

FIG. 1 is a schematic pictorial illustration of a system 20 for cardiac ablation treatment, in accordance with an embodiment of the present invention. An operator 28 (such as an interventional cardiologist) inserts a catheter 22 via the vascular system of a patient 26 into a chamber of the patient's heart 24. For example, to treat atrial fibrillation, the operator may advance the catheter into the left atrium and bring a distal end 30 of the catheter into contact with myocardial tissue that is to be ablated.

Catheter 22 is connected at its proximal end to a console 32, which is controlled by operator 28 to apply and monitor the desired treatment. Console 32 comprises an RF energy generator 34, which supplies electrical power via catheter 22 to distal end 30 in order to ablate the target tissue. Monitoring circuitry 36 tracks the temperature of the tissue at distal end 30 by processing the outputs of temperature sensors in the distal end, as described below. An irrigation pump 38 supplies a cooling fluid, such as saline solution, through catheter to irrigate distal end 30. On the basis of information provided by monitoring circuitry 36, console 32 may control the power applied by RF energy generator 34 and/or the flow of fluid provided by pump 38, either automatically or in response to inputs by operator 28.

System 20 may be based on the above-mentioned CARTO system, for example, which provides extensive facilities to support navigation and control of catheter 22. These system facilities, however, including details of the monitoring and control functions of monitoring circuitry 36 and console 32 generally, are beyond the scope of the present patent application.

Figure 2A:
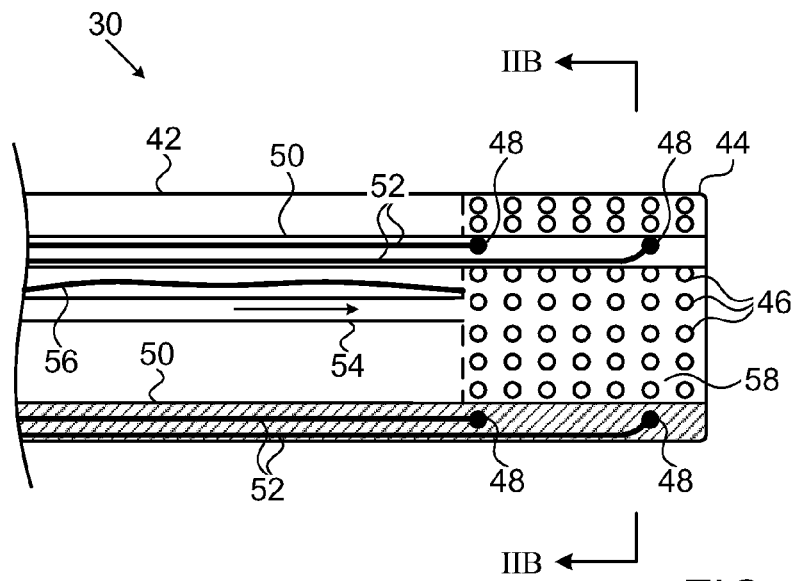
FIG. 2A is a schematic, sectional view of a catheter tip, in accordance with an embodiment of the present invention.
Figure 2B:
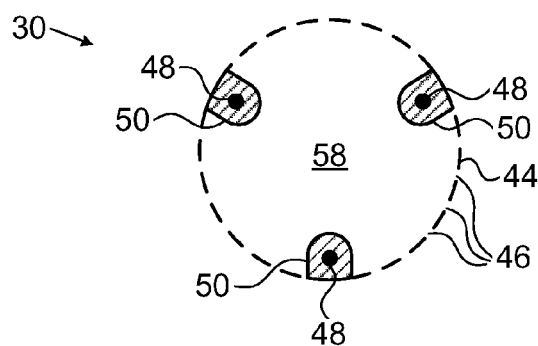
FIG. 2B is a schematic, cross-sectional view of the catheter tip of FIG. 2A.

FIGS. 2A and 2B schematically illustrate distal end 30 of catheter 22, in accordance with an embodiment of the present invention. FIG. 2A is a sectional view along the length of the catheter, while FIG. 2B is a cross-sectional view along the cut IIB-IIB that is marked in FIG. 2A. An insertion tube 42 extends along the length of the catheter and is connected at its distal end to a conductive cap 44. Typically, insertion tube 42 comprises a flexible, biocompatible polymer, while cap 44 comprises a biocompatible metal suitable to serve as an ablation electrode, such as gold or platinum, for example. Cap 44 is perforated by an array of irrigation apertures 46, which open from the outer surface of the cap into an inner cavity 58 within the cap. For typical intracardiac ablation applications, the diameter of cap 44 may be about 2.5 mm, with a wall thickness of about 0.2 mm and apertures 46 of diameter 0.1-0.2 mm. The above dimensions and materials are described by way of example, however, and other suitable materials, with features of larger or smaller dimensions, may similarly be used.

Cavity 58 is in fluid communication with a lumen 54, which runs through the length of insertion tube 42. Lumen 54 is coupled at its proximal end to irrigation pump 38, and thus conveys irrigation fluid to cavity 58, from which the fluid flows out through apertures 46. An electrical conductor 56 conveys electrical energy from RF generator 34, through insertion tube 42, to cap 44, and thus energizes the cap to ablate myocardial tissue with which the cap is in contact. During ablation, the fluid flowing out through apertures 46 irrigates the tissue under treatment.

Temperature sensors 48 are mounted within conductive cap 44 at locations that are arrayed around the distal tip of the catheter, both axially and circumferentially. In this example, cap 44 contains six sensors, with one group in a distal location, close to the tip, and the other group in a slightly more proximal location. This distribution is shown only by way of example, however, and greater or smaller numbers of sensors may be mounted in any suitable locations within the cap. Sensors 48 may comprise thermocouples, thermistors, or any other suitable type of miniature temperature sensor. These sensors are connected by leads 52 running through the length of insertion tube 42 to provide temperature signals to monitoring circuitry 36.

Temperature sensors 48 are mounted within ribs 50 inside cap 44. The ribs are typically an integral part of cap 44 and may be made from the same material as the outer surface of the cap or from some other suitable type of metal, which is physically and thermally bonded to the cap. The diameter of the ribs may be a few tenths of a millimeter in the present example. The integral construction of ribs 50 with cap 44 causes sensors 48 to be in thermal communication with the outer surface of the cap, i.e., the temperature inside ribs 50 closely tracks the temperature of the outer surface. The ribs are thick enough to thermally insulate these sensors from the irrigation fluid in cavity 58. As a result, temperature sensors 48 measure the true temperature of the outer surface of cap 44, which most accurately reflects the temperature of the tissue with which the cap is in contact.

Typically, distal end 30 contains other functional components, which are outside the scope of the present disclosure and are therefore omitted for the sake of simplicity. For example, the distal end of the catheter may contain steering wires, as well as sensors of other types, such as a position sensor and/or a contact force sensor. A catheter containing sensors of these sorts is described, for example, in U.S. Patent Application Publication 2009/0138007, whose disclosure is incorporated herein by reference.

Figure 3:
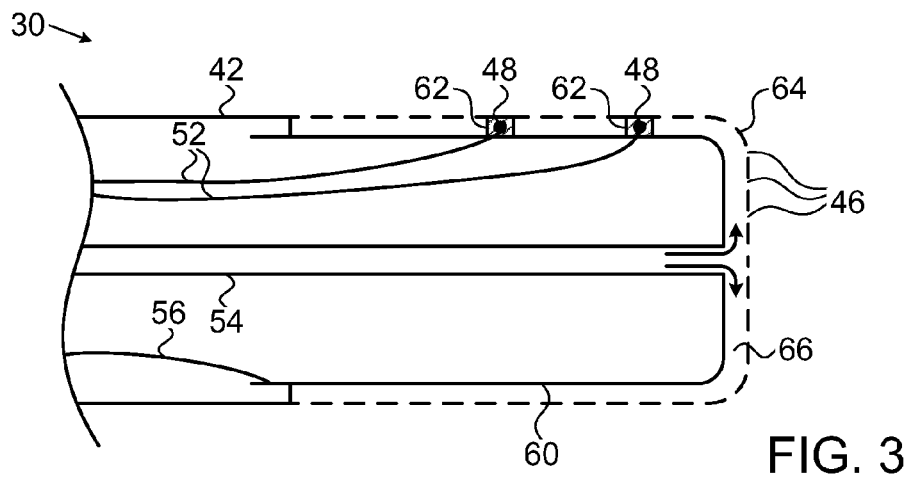
FIG. 3 is a schematic, sectional view of a catheter tip, in accordance with another embodiment of the present invention.

FIG. 3 is a schematic sectional view of distal end 30, in accordance with another embodiment of the present invention. Elements of this embodiment that are similar to corresponding elements in the embodiment of FIGS. 2A and 2B are marked with the same indicator numbers. In the embodiment of FIG. 3, a conductive, perforated cap 64, attached to the distal end of insertion tube 42, is designed to have very low thermal capacity, and sensors 48 are held in contact with cap 64. As a result of this configuration, the temperature of cap 64 more closely track changes in the actual tissue temperature, and sensors 48 more closely track the temperature of the outer surface of cap 64. Sensors 48 thus provide a more accurate, timely indication of changes in the temperature of the tissue with which cap 64 is in contact.

As illustrated in FIG. 3, cap 64 contains an inner wall 60, which is not perforated, in close proximity and parallel to the cap. Lumen 54 supplies irrigation fluid to a cavity 66 that is formed between cap 64 and wall 60, and the irrigation fluid exits this cavity through apertures 46 in cap 64. Typically, cap 64 and wall comprise thin shells of metallic material and are held apart by small metallic spacers 62, around which the fluid is able to flow within cavity 66. These spacers may be distributed within cap in any suitable arrangement, for example in pairs (like the pair shown in FIG. 3) of axially-spaced sensors at different circumferential locations. Spacers 62 also hold temperature sensors 48 in thermal communication with the outer surface of cap 64, while insulating the sensors from the surrounding irrigation fluid in cavity 66. Even without the insulating effect of spacers 62, the effect of the irrigation fluid temperature on sensors 48 in this embodiment is minimal due to the small volume of cavity (relative to cavity 58 in the preceding embodiment, for example).

In a configuration suitable for intracardiac ablation, cap 64 has an outer diameter of about 2.5 mm and a similar length. The thickness of both cap 64 and wall 60 is about 100 µm, while apertures 46 have a diameter in the range of 25-100 µm. Although cap 64 and wall 60 are very thin, the mechanical integrity of the entire structure is maintained by connecting the cap and wall together with spacers 62.

Figure 4A:
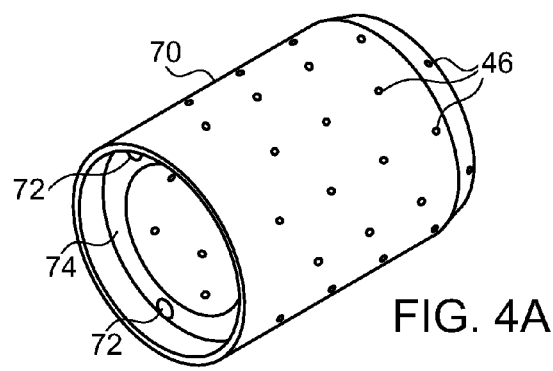
FIG. 4A is a schematic, pictorial illustration of a catheter cap, in accordance with yet another embodiment of the present invention.
Figure 4B:
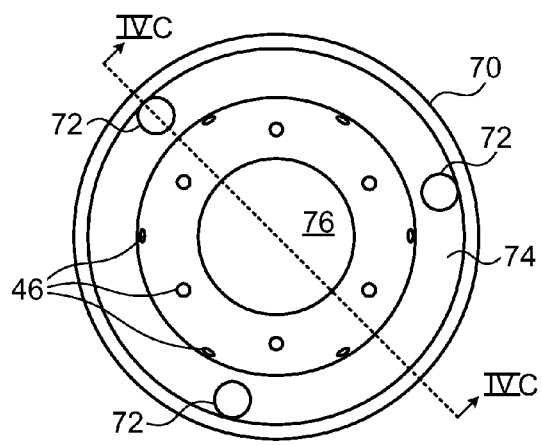
FIG. 4B is a schematic end view of the catheter cap of FIG. 4A.
Figure 4C:
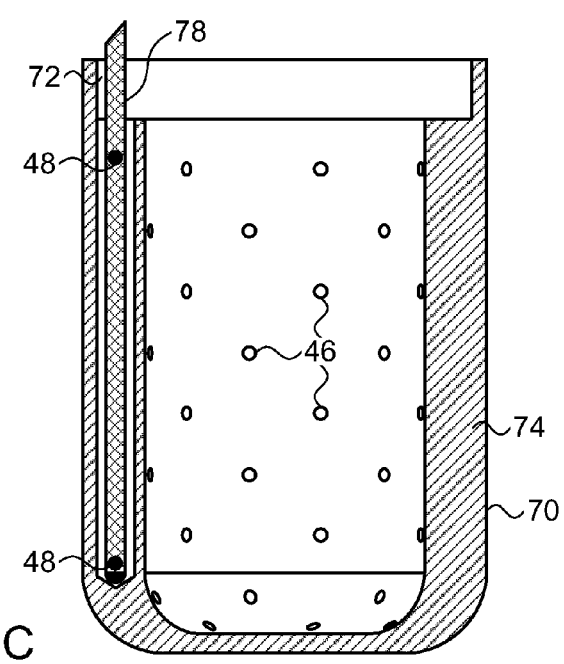
FIG. 4C is a schematic, sectional view of the catheter cap of FIGS. 4A and 4B.

FIGS. 4A-4C schematically illustrate a catheter cap 70, in accordance with yet another embodiment of the present invention. Cap 70 may be used at distal end 30 of catheter 22 in place of the caps shown in the preceding embodiments. FIG. 4A is a schematic, pictorial illustration of cap 70, while FIG. 4B is a schematic end view showing the interior of the cap, and FIG. 4C is a sectional view taken along the line IVC-IVC in FIG. 4B.

Cap 70 comprises a side wall 74 that is relatively thick, on the order of 0.4 mm thick, in order to provide the desired thermal insulation between temperature sensors 48 and the irrigation fluid inside a central cavity 76 of the tip. As in the preceding embodiments, the irrigation fluid exits cavity 76 through apertures 46. Sensors 48 are mounted in hollow tubes 78, which are filled with a suitable glue, such as epoxy and fitted into longitudinal bores 72 in side wall 74. Tubes 78 may comprise a suitable plastic material, such as polyimide, and may be held in place by a suitable glue, such as epoxy. This arrangement provides an array of six sensors as in the preceding embodiments, with possible advantages of greater ease of manufacture and durability.

Although a number of particular implementation examples have been shown and described above, alternative implementations of the principles embodied in these examples will be apparent to those skilled in the art after reading the foregoing description and are considered to be within the scope of the present invention. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical probe, comprising:
   an insertion tube having a distal end configured for insertion into a body of a patient and containing a lumen for conveying an irrigation fluid and an electrical conductor for conveying electrical energy;
   a conductive cap attached to the distal end of the insertion tube and coupled electrically to the electrical conductor, wherein the conductive cap has an outer surface perforated by multiple apertures and defines an inner cavity in fluid communication with the lumen of the insertion tube so as to permit the irrigation fluid from the lumen to flow out of the cap through the apertures and a plurality of ribs integrally constructed into an inner surface of the conductive cap; and
   a plurality of temperature sensors, wherein a temperature sensor is mounted within each rib integrally formed into the inner surface of the conductive cap in thermal communication with the outer surface and are thermally insulated from the irrigation fluid in the inner cavity.

2. Medical apparatus, comprising:
   a probe, which is configured for insertion into a body of a patient and comprises: an insertion tube having distal and proximal ends and containing a lumen for conveying an irrigation fluid and an electrical conductor for conveying electrical energy;
   a conductive cap attached to the distal end of the insertion tube and coupled electrically to the electrical conductor, wherein the conductive cap has an outer surface perforated by multiple apertures and defines an inner cavity in fluid communication with the lumen of the insertion tube so as to permit the irrigation fluid from the lumen to flow out of the cap through the apertures, wherein the cap comprises multiple ribs internal to the outer surface, wherein the ribs are integrally formed on an inner surface of the conductive cap from the same material as the conductive cap; and
   a plurality of temperature sensors in each of the multiple ribs, which are mounted within the conductive cap in thermal communication with the outer surface and are thermally insulated from the irrigation fluid in the inner cavity;
   a pump, coupled to the lumen at the proximal end of the insertion tube so as to supply the irrigation fluid to the probe;
   a power generator, coupled to the electrical conductor at the proximal end of the insertion tube so as to provide the electrical energy to the conductive cap; and
   monitoring circuitry, which is connected to receive temperature signals from the temperature sensors so as to monitor a temperature of the cap.

* * * * *